United States Patent [19]  
Budzak et al.

[11] 3,933,165  
[45] Jan. 20, 1976

[54] APPARATUS FOR OCTANE MONITORING
[75] Inventors: Paul A. Budzak, Cheswick; Russell M. Clinton, III, Gibsonia, both of Pa.
[73] Assignee: Gulf Research & Development Company, Pittsburgh, Pa.
[22] Filed: Aug. 20, 1974
[21] Appl. No.: 499,060

[52] U.S. Cl. ........................ 137/625.48; 73/422 GC
[51] Int. Cl.² ...................... G01N 1/00; F16K 11/06
[58] Field of Search... 73/422 GC; 137/197, 625.48, 137/625.66

[56] References Cited  
UNITED STATES PATENTS

| 1,464,110 | 8/1923 | Ramsey | 137/197 X |
| 2,601,216 | 6/1952 | White et al. | 137/197 |
| 3,160,015 | 12/1964 | Charlton et al. | 73/422 GC |
| 3,479,880 | 11/1969 | Motter et al. | 73/422 GC |
| 3,550,847 | 12/1970 | Scott | 137/625.66 X |

Primary Examiner—Henry T. Klinksiek

[57] ABSTRACT

An octane analyzer for monitoring the octane of a gasoline stream in which a sample of the gasoline stream is periodically injected into a reactor containing oxygen and maintained at a temperature at which mild reaction results. The time required for initiation of the mild reaction or the severity of the mild reaction is measured and correlated with octane number. Means are provided to charge a reproducible sample into the reaction by maintaining the sample under a pressure holding it in the liquid phase and delivering it into a chamber in which the pressure is reduced to cause vaporization of the sample. The chamber is packed with finely divided material that holds gasoline in the liquid phase in the chamber.

5 Claims, 3 Drawing Figures

APPARATUS FOR OCTANE MONITORING

This invention relates to the monitoring of a characteristic of a hydrocarbon fuel and more particularly to a method and apparatus for monitoring the octane number of a refinery gasoline stream.

Gasoline is ordinarily manufactured at refineries by processing various petroleum fractions to produce streams, hereinafter referred to as "gasoline streams", having boiling points in the gasoline boiling range. The various gasoline streams may be straight-run gasoline, reformer gasoline cracked gasoline, alkylate, etc. The gasoline streams are then blended in proportions that will give a gasoline product meeting the desired gasoline specifications, and particularly having the desired octane number. The usual procedure is to blend the gasoline streams to produce a gasoline having an octane number lower than the specification gasoline product and make the final correction of octane number by the addition of tetraethyl lead.

In the operation of the refinery, an effort is made to operate each of the processing units to produce a gasoline stream having a target octane number that will balance the production of the several gasoline streams with the requirements for blending gasoline product of the desired specifications. Then the gasoline streams can be blended in-line as they are produced by the processing units. Ordinarily, variations in the feedstock or conditions in the processing units cause variations in the blending characteristics of the gasoline streams which limit or prevent in-line blending. The customary practice has been to deliver the gasoline streams to storage, sample the contents of the storage tanks and measure their octane numbers, and then blend the gasoline in an essentially batch process. Because of the variations in the specification of the gasoline streams delivered into storage over the period a storage tank is being filled, it is frequently necessary to mix the contents of the storage tank for long periods to obtain a uniform composition throughout the storage tank. The batch blending operation is expensive both in its requirements of storage capacity and manpower.

It is desirable, in order to reduce the costs of gasoline blending, to blend directly gasoline streams from the different processing units to produce a gasoline product having the desired specifications. To accomplish the desired in-line blending it is essential that the octane number of the various gasoline streams be monitored, then the proportions of the various gasoline streams can be altered as required by variations in the properties of the gasoline streams. The standard method of determination of the octane number of a gasoline stream in an engine is too costly to be an effective method of octane determination for in-line blending.

One process that has been developed for monitoring the octane number of a gasoline stream is described in U.S. Pat. No. 3,463,613 of E. R. Fenske et al. In the process described in that patent, a gasoline stream and an oxygen-containing gas are passed continuously through a reactor tube maintained at a temperature at which a cool flame develops as a result of the oxidation of the gasoline stream. The pressure maintained on the reactor tube is controlled to maintain the cool flame at a fixed position in the reactor tube. A correlation between the pressure required to maintain the flame at a fixed position and the octane number of the gasoline stream is used to convert the pressure reading to octane number. The process described in U.S. Pat. No. 3,463,613 is not wholly satisfactory. The method is highly sensitive to the quality of the gasoline stream. The term "quality" as used herein is used to designate the particular types of compounds in the gasoline stream and will depend upon the type of processing unit in which the gasoline stream is produced. Moreover, the continuous flow of gasoline through the reactor tube results in the formation of deposits which causes an alteration in the characteristics of the testing apparatus over a period of time.

Another method of monitoring the octane number of the gasoline stream is described in U.S. Pat. No. 3,738,810 of Clinton and Puzniak. In the process described in that patent, a sample of the gasoline stream is injected periodically into a reactor through which an oxygen-containing gas flows at a temperature ordinarily in the range of 275° C. to 350° C. that causes a mild oxidation reaction. The severity of the mild reaction is safely below the range at which an explosion occurs. The severity and/or induction period of the mild reaction is measured and correlated with the octane number whereby the severity measurement or induction period can be used directly as an indication of the octane number of the gasoline stream. The induction period may be measured by measuring the time until the reaction is initiated, as indicated by an increase in the temperature in the reactor. The severity is measured as the magnitude of a temperature or pressure pulse. Another measure of the severity of reaction that can be used is a determination of the rate of temperature increase once the reaction is initiated.

The process described in U.S. Pat. No. 3,738,810 has been found to give an improved monitoring of an octane number of a gasoline stream. It is important to the process of U.S. Pat. No. 3,738,810 that the gasoline sample delivered into the reactor be reproducible in size, phase and concentration in the oxygen-containing gas.

This invention resides in apparatus and a method adapted to inject a sample of a gasoline stream periodically into a reactor containing an oxygen-containing gas in an oven maintained at an elevated temperature. The sample is displaced in the liquid phase by a carrier gas into a chamber filled with finely divided solid material adapted to hold in the chamber by capillary action that part of the gasoline that remains in the liquid phase and thereby prevent delivery into the reactor of droplets of liquid gasoline.

Following displacement of the complete sample of the gasoline into the chamber, carrier gas flows through the chamber and then into the reactor to evaporate and sweep into the reactor that part of the gasoline sample that is held by capillary action. The finely divided material provides a large surface area from which reproducible evaporation occurs.

Figure 1:
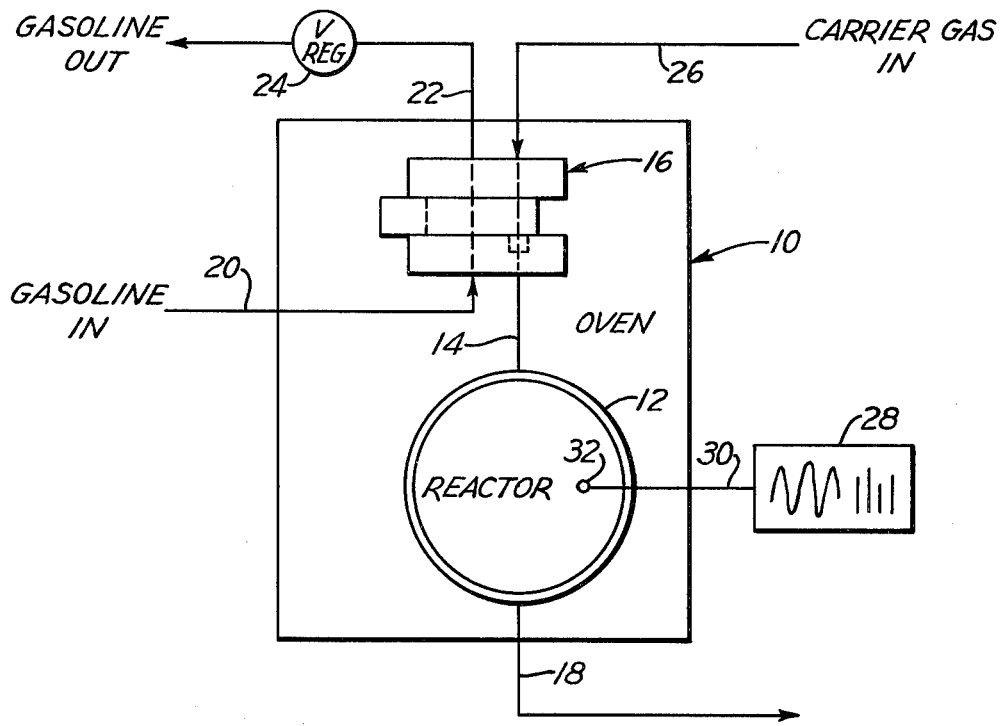
FIG. 1 is a diagrammatic illustration of apparatus useful in the monitoring of the octane number of a gasoline stream in accordance with this invention.

Referring to FIG. 1, an oven indicated generally by reference numeral 10 is shown enclosing a reactor 12. Oven 10 is provided with suitable heating and control means to maintain the oven at the desired temperature which is ordinarily 60° C. to 90° C. and preferably about 75° C. Reactor 12 can, for example, be a stainless steel or glass sphere heavily insulated and provided with any suitable heating device such as electrical heating elements to maintain the temperature within the reactor at a constant temperature between 275° C. and 350° C. between sample injections. Reactor 12 is connected by an inlet line 14 to a sampling valve indicated in FIG. 1 generally by reference numeral 16. A vent line 18 from the reactor maintains the reactor at substantantially atmospheric pressure and provides an outlet for the reactor. A gasoline stream inlet line 20 is connected into the gasoline stream produced by a processing unit to provide a continuous flow of a slip stream through the sampling valve of the gasoline stream to be monitored. The gasoline circulated through the sampling valve is discharged through an outlet line 22. A regulating valve 24 in the outlet line maintains the pressure in lines 20 and 22 high enough to prevent vaporization of gasoline at the temperatures existing within the oven 10.

A carrier gas supply line 26 from a source, not shown in the drawings, preferably at a temperature of approximately 75° C., is connected into sampling valve 16 and communicates through passages in that valve with the inlet line 14. It is essential to the mild oxidation reaction that occurs in reactor 12 that an oxygen-containing gas be delivered into the reactor. It is preferred, therefore, that the carrier gas delivered to the sampling valve 16 be an oxygen-containing gas. Air is a preferred oxygen-containing gas. If a gas that does not include oxygen is used as the carrier gas, it will be necessary to supply oxygen into the reactor from a source other than the carrier gas.

A recorder 28 is provided to give an indication of the severity of the reaction that occurs within reactor 12. The recorder and the system for operating it are described in detail in U.S. Pat. No. 3,738,810 of Clinton et al. As indicated in U.S. Pat. No. 3,738,810, the recorder can be adapted to indicate the parameters of severity or induction period of the reaction that can be correlated with the octane number of the gasoline. For example, the recorder can be constructed to indicate the time required after injection of a sample of the gasoline stream for initiation of the oxidation reaction or to indicate the magnitude of a temperature or pressure pulse. For purposes of illustration, severity is used to indicate the octane number of the gasoline. The details of the recorder and the timing mechanism are not a part of this invention and will not be further described except to indicate a connection, such as by a lead line 20, of the recorder to a thermocouple 32 in the reactor.

Figures 2, 3:
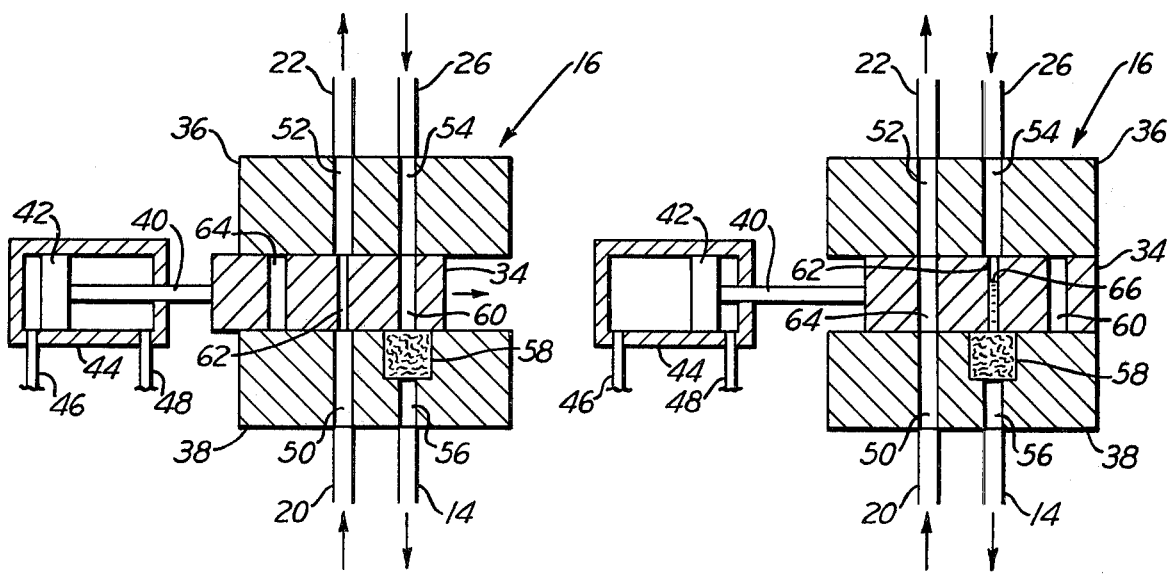
FIG. 2 is a diagrammatic vertical sectional view of an injection valve used in this invention in the position it occupies between octane determinations.
FIG. 3 is a diagrammatic vertical sectional view of the sampling valve illustrated in FIG. 2 in position for injecting a sample of the gasoline stream into the reactor of the octane monitoring apparatus.

Referring to FIG. 2 of the drawings, sampling valve 16 includes a sliding block 34 adapted to slide between a top block 36 and a bottom block 38. Sliding block 34 is preferably constructed of Teflon and is in the form of a rectangular block adapted to engage and seal against the flat top surface of bottom block 38 and the flat bottom surface of top block 36. Suitable means such as an adjustably compressed helical spring, not shown, engaging the top surface of top block 36 urges the blocks together to prevent leakage. The movement of the sliding block 34 between top block 36 and bottom block 38 is controlled by a connecting rod 40 driven by suitable means. In the apparatus illustrated in the drawings utilizing pneumatic controls to operate the sampling valve, connecting rod 40 is connected to a piston 42 in a cylinder 44. Air lines 46 and 48 extend from cylinder 44 to air control and timing means, not shown in the drawings, for periodic reciprocation of the sliding block 34 between the circulating position illustrated in FIG. 2 and the sample injection position illustrated in FIG. 3.

Bottom block 38 has a gasoline passage 50 extending through it and opening at the top surface of the bottom block. Passage 50 is connected at its lower end to gasoline inlet line 20. A gasoline passage 52 in top block 36 has an inlet in the bottom surface of the block in alignment with passage 50 and an outlet connected with discharge line 22. A carrier gas passage 54 connected to carrier gas supply line 26 extends through top block 36 and has an outlet in the bottom surface of the top block. A sample passage 56 in lower block 38 connected at its lower end with inlet line 14 to the reactor is in vertical alignment with carrier gas passage 54. At the upper end of sample passage 56 is an enlarged chamber 58 which extends to the upper surface of lower block 38. Chamber 58 is filled with a finely divided material such as glass wool, stainless steel shavings, or other particulate material that will provide sufficient surface and small enough openings to hold within the chamber by capillary action that portion of the gasoline sample that is not vaporized before the carrier gas following the sample enters the chamber 58. A permeable monolithic block can be used in chamber 58.

Sliding block 34 has a vertical carrier gas passage 60 and a vertical gasoline sample passage 62 extending through it. Those passages are spaced apart a distance equal to the spacing between the openings of passages 52 and 54 through the bottom surface of the top block 36. In the preferred embodiment of the invention illustrated in the drawings, there is also a gasoline circulating passage 64 extending vertically through the sliding block 34 located on the side of sample passage 62 opposite passage 60 so that circulating passage 64 communicates with passages 50 and 52 when the sample valve is in the injection position illustrated in FIG. 3.

As shown in FIGS. 2 and 3, it is preferred that the diameter of passages 60 and 64 be larger than the diameter of the passage 62. The diameter of the passage 62 is designed to provide a volume that will give a sample of the desired size. Small samples, preferably having a volume in the range of 2 to 25 microliters, are used in the octane monitoring process. The dimensions of inlet line 20 and carrier gas supply line 26 are such that the gasoline stream flowing through passage 62 and the carrier gas flowing through passage 60 are substantially at the oven temperature. The chamber 58 has a diameter and volume large enough to avoid substantial blow back of the gasoline sample into the carrier gas line when the pressure on the sample is reduced, and a surface area adequate to hold the liquid that is not vaporized ahead of the carrier gas in a thin film whereby droplets of liquid gasoline are not carried to the reactor by the carrier gas. Because much of the gasoline sample will remain liquid at the temperature of the sample valve, a chamber 58 having a diameter at least four times the diameter of sample passage 62 is adequate.

In the operation of the apparatus of this invention, the oven is raised to a temperature of approximately 75° C. for a period adequate to raise the temperature of the valve 16 and the lines 20 and 26 to the desired temperature. A slip stream of the gasoline stream to be monitored is delivered through line 20 to the sampling valve 16 and passes through passages 50, 62 and 52 into discharge line 22. Pressure regulating valve 24 maintains the pressure in line 22 high enough to prevent vaporization of the gasoline stream. The gasoline flowing through line 22 is discharged through valve 24 to suitable disposal. The carrier gas, preferably air, is delivered through line 26 into passage 54. The gas then flows through passage 60 into chamber 58 and then through passage 56 into line 14 and into the reactor 12. Meanwhile, the temperature of the reactor 12 is raised to a temperature in the range of 275° C. to 350° C. by suitable electric heating elements, not shown.

Periodically piston 42 is moved in cylinder 44 from the position shown in FIG. 2 to the position shown in FIG. 3 to place sample passage 62 in alignment and communication with carrier gas passage 54 and with chamber 58. Gasoline trapped in sample passage 62 as the sliding block 34 moves to the right is displaced by the carrier gas into chamber 58. The gasoline interrupts the flow of carrier gas to the chamber 58 until the carrier gas has forced the upper surface 66 of the sample downward into chamber 58. The frequency of delivering a sample of gasoline into the chamber may range from about once every three minutes to about once every 15 minutes, or even less frequently. There is, of course, no limit on the length of the period between octane determinations, but the advantages and objects of octane monitoring are not fully realized if the sampling is too infrequent. The minimum time between samplings is determined by the time required for effective purging of hydrocarbons and reaction products from the chamber 58 and especially from the reactor 12. A frequency of one octane determination every five minutes will give an excellent balance of frequent octane determinations and effective and sure purging of the reactor. While the sample valve is in the injection position illustrated in FIG. 3, gasoline circulates through circulating passage 64 to make unnecessary a long period of purging sample lines after each injection.

Because of the reduced pressure in chamber 58 as compared with line 22, the gasoline begins vaporization immediately upon flowing into the chamber from passage 62. Thus, a slug of hydrocarbon vapor substantially undiluted by carrier gas is quickly delivered into reactor 12. The characteristics of the gasoline will determine the time required for the reaction between the gasoline and oxygen in the reactor to raise the temperature in the reactor to give a signal that through the correlation shows the octane number of the gasoline. The time required will depend upon the temperature at which the reactor is maintained and the octane number of the gasoline stream. The time for the reaction to proceed far enough to give a signal usually is in the range of 1 to 20 seconds.

It is a feature of this invention that the hydrocarbon vapors initially flowing into the reactor 12 are not entrained in the carrier gas. The plug of the gasoline sample in passage 62 acts as a barrier momentarily interrupting the flow of the carrier gas into chamber 58 when the sampling valve is in the position illustrated in FIG. 3. After the full gasoline sample has been displaced from passage 62, the carrier gas flows into chamber 58 and quickly evaporates and entrains to the reactor any of the sample of gasoline that may be remaining in the chamber. Thus, the sample of gasoline is delivered into the reactor in the form of a reproducible wave that is substantially square at its front end to provide a sharp starting point for the reaction with the oxygen-containing gas in the reactor quickly followed by a mixture rich in heavier fractions of the gasoline such that the hydrocarbons in the reactor during the induction period are indicative of the properties of the gasoline stream.

After the sample has been discharged from passage 62, the sliding block 34 is returned from the position shown in FIG. 3 to the position shown in FIG. 2. A slip strem of the gasoline stream is then circulated through inlet line 20, the sample passage 62 in sample valve 16 and discharge line 22 until it is time for another sample. During the period that sample valve 16 is in the position shown in FIG. 2, the carrier gas is delivered through passages 54, 60 and 56 into the reactor 12 to complete the reaction of gasoline delivered to the reactor 12 and condition the reactor for the next sample of gasoline injected into it. Reaction products and the carrier gas are discharged through vent line 18. If the carrier gas used should be an inert gas, such as nitrogen, it will then be necessary to provide a separate line for delivery into reactor 12 of the oxygen-containing gas needed for the reaction.

This invention provides means and a method for the injection into a reactor containing an oxygen-containing gas of reproducible samples of gasoline vapors having a high concentration of the gasoline vapors. The vapors delivered into the reactor are initially substantially devoid of carrier gas, thereby eliminating variations in the concentration of the carrier gas in the sample that might occur if the flow of carrier gas to the reactor were not interrupted and the carrier gas were used to sweep the entire sample into the reactor. The reproducibility of the front edge of the sample that is injected into the reactor contributes to accurate monitoring of the gasoline. The large surface area of the wicking material in the chamber speeds the evaporation of heavier fractions in the gasoline sample and also prevents delivery of droplets of liquid gasoline into the reactor. Rapid evaporation of the heavier fractions of the sample results in the hydrocarbons in the reactor during the induction period being representative of the gasoline stream sampled. It is highly desirable to avoid the delivery of droplets into the reactor because the size of the droplets cannot be controlled accurately; consequently, the droplets may evaporate at widely varying rates.

The octane monitor of this invention can be used to monitor the octane number of blended gasoline as well as to monitor the individual gasoline streams making up the blend. It is particularly useful in blending unleaded gasolines because final correction of the octane number by increasing or decreasing the concentration of lead tetraethyl is not possible.

We claim:

1. Apparatus for charging a gasoline stream to a reactor in which the gasoline is mildly reacted with an oxygen-containing gas for monitoring the octane number of the gasoline, comprising a sampling valve including a first guide block having a guide surface, a second guide block spaced from the first guide block and having a guide surface spaced from and parallel to the guide surface of the first guide block, a slider block between the guide blocks constructed and arranged to slidably and sealingly engage the guide surfaces on the first guide block and second guide block, gasoline circulating passages through each of the guide blocks opening through the guide surfaces thereof, a carrier gas passage extending through the first guide block and opening through the guide surface thereof, a sample delivery passage through the second guide block opening at the guide surface thereof, a gasoline sampling passage through the slider block constructed and arranged to communicate with the gasoline circulating passages when the slider block is in a gasoline circulating position, a carrier gas passage through the slider block spaced from the gasoline sampling passage oriented whereby the carrier gas passage in the slider block communicates with the carrier gas passage in the first guide block and the sample delivery passage in the second guide block when the slider block is in the gasoline circulating position, means connected to the slider block for periodically moving the slider block from the gasoline circulating position to a sample delivery position placing the gasoline sampling passage in the slider block in communication with the sample delivery passage in the second guide block and the carrier gas passage in the first guide b'ock, a chamber of large volume and cross-sectional area relative to the volume and cross-sectional area of the gasoline sampling passage adjacent the guide surface of the second guide block forming a part of the sample delivery passage in the second guide block, and wicking means in the chamber.

2. Apparatus as set forth in claim 1 in which the enlarged chamber has a diameter at least about four times the diameter of the gasoline sampling passage.

3. Apparatus for charging a sample of a gasoline stream into a reactor maintained at substantially atmospheric pressure and containing an oxygen-containing gas for monitoring the octane number of the gasoline comprising a first guide block and a second guide block spaced from and parallel to the first guide block, a slider block positioned between the guide blocks and adapted to sealingly and slidably engage the guide blocks, means connected to the slider block for reciprocating the slider block between a gasoline circulating position and a sample delivery position, a gasoline sampling passage in the slider block, gasoline circulating passages through the guide blocks in communication with one another and with the gasoline sampling passage when the slider block is in the gasoline circulating position, pressure regulating means constructed and arranged to maintain a pressure in the gasoline circulating passages adapted to keep gasoline therein in the liquid phase, a carrier gas passage through the first guide block, a sample delivery passage through the second guide block, a carrier gas passage through the slider block positioned to communicate with the carrier gas passage in the first guide block and the sample delivery passage when the slider block is in the gasoline circulating position, conduit means extending from the sample delivery passage to the reactor, a chamber of large volume and cross-sectional area relative to the volume and cross-sectional area of the gasoline sampling passage in the sample delivery passage adjacent the slider block, and wicking means in the enlarged chamber, said gasoline sampling passage communicating with the carrier gas passage and sample delivery passage when the slider block is in the sample delivery position.

4. Apparatus as set forth in claim 3 including heating and control means for maintaining the slider block and guide blocks at a temperature in the range of 60° to 90° C.

5. Apparatus as set forth in claim 3 including a gasoline circulating passage through the slider block positioned to communicate with the circulating passages in the guide blocks when the slider block is in the sample delivery position.

\* \* \* \* \*